United States Patent
Chakrabarty et al.

(10) Patent No.: US 10,266,573 B2
(45) Date of Patent: *Apr. 23, 2019

(54) CYTOTOXIC FACTORS FOR MODULATING CELL DEATH

(75) Inventors: Ananda M. Chakrabarty, Villa Park, IL (US); Tapas K. Das Gupta, River Forest, IL (US); Vasu Punji, Chicago, IL (US); Olga Zaborina, Brookfield, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/123,131

(22) Filed: May 19, 2008

(65) Prior Publication Data

US 2009/0137468 A1    May 28, 2009

Related U.S. Application Data

(63) Continuation of application No. 11/485,252, filed on Jul. 13, 2006, which is a continuation of application No. 10/047,710, filed on Jan. 15, 2002, now Pat. No. 7,084,105.

(60) Provisional application No. 60/269,133, filed on Feb. 15, 2001.

(51) Int. Cl.
| | | |
|---|---|---|
| A61K 38/00 | (2006.01) |
| C07K 14/35 | (2006.01) |
| G01N 33/50 | (2006.01) |
| C07K 14/195 | (2006.01) |
| G01N 33/569 | (2006.01) |

(52) U.S. Cl.
CPC ............ *C07K 14/35* (2013.01); *C07K 14/195* (2013.01); *G01N 33/5011* (2013.01); *G01N 33/569* (2013.01); *A61K 38/00* (2013.01); *G01N 2510/00* (2013.01)

(58) Field of Classification Search
CPC .................................................. A61K 38/164
See application file for complete search history.

(56) References Cited

U.S. PATENT DOCUMENTS

| | | | |
|---|---|---|---|
| 5,681,810 | A | 10/1997 | Villemez et al. |
| 5,789,389 | A | 8/1998 | Tarasewicz |
| 5,972,899 | A | 10/1999 | Zychlinsky et al. |
| 6,387,695 | B1 | 5/2002 | Evans et al. |
| 2008/0221015 | A1 | 9/2008 | Chaudhari et al. |

FOREIGN PATENT DOCUMENTS

| | | | |
|---|---|---|---|
| WO | 19990004986 | | 10/1999 |
| WO | WO 99/49860 | * | 10/1999 |
| WO | 02076380 A2 | | 10/2002 |

OTHER PUBLICATIONS

Strange et al., Acta crystallographica. Section D, Biological crystallography (Denmark), 1994, 50 (Pt 1), p. 37-9.*
Yamada, T., et al. Cellular Microbiology, 7(10): 1418-1431, 2005.*
Van de Kamp, M., et al, Eur. J. Biochem., 194: 109-118, 1990.*
Parr, S.R., et al., Biochem. J. 157: 423-430, 1976.*
Buckley, Christopher D, Letter of Nature; 397: 534-539 (1999).
Zaborina, Olga, Mal. Microbiology, 31(5) 1333-1343 (1999).
Yamada, Tohru et al., "Bacterial Redox Protein Azurin, Tumor Suppressor Protein p53, and Regression of Cancer", Proceedings of the National Academy of Sciences of the United States of American 99(22) 14098-14103 (2004) XP002486971.
Gough, Julian et al., "The linked Conversation of Structure and Function in a Family of High Diversity: The monomeric Cupredoxins", Structure (Cambridge) 12 (6) 917-925 (2004) XP002486972.
PCT International Application No. PT/US02/01408—International Search Report.
Anonymous: Database EMBL Online Nov. 1, 1997 XP002306632 abstract.
Anonymous: Database EMBL Online Mar. 1, 1992 XP002306633 abstract.
Anonymous: Database EMBL Online Feb. 1, 1991 XP002306634 abstract.
Alexandroff, Anton B. et al., The Lancet, vol. 353 1689-1694 (May 15, 1999).
Confer, A. W. and Durham, Janet A., Am. J. Res. vol. 53, No. 5, pp. 646-652 (1992).
Cutruzzola, F. et al., J. Inorganic Chemistry, 88 pp. 353-361 (2002).
Dang, L. H. et al., Proc. Nat. Acad. Sci. USA, 98, 15155-15160 (2001).
Goto, M. et al., Mol. Bio., 47(s) pp. 549-559 (2003).
Hunter, Christopher A. et al., The J. of Immunology, 166: 5878-5881 (2001).
Jain, R. K., et al., Proc. Nat. Acad. Sci. USA 98, 14748-14750 (2001).
Kim, David H. et al., The J. of Clinical Investigation, 105(7) 837-839 (2000).
Kukimoto et al., FEBS Letters, 394 pp. 87-90 (1996).
Melnikov, A. et al., Mol. Microbiol. 36:1481-1493 (2000).
Murphy, L.M. et al., J. Mol. Biol., 315: 859-71 (2002).
O'Donnell, Michael A., Tibtech, vol. 15, 512-517 (Dec. 1997).
Paglia, Paola et al., The J. of Immunology, 166: 5878-5881 (2001).
Pawelek, John H. et al., Cancer Research, vol. 57, 4537-4544 (1997).

(Continued)

*Primary Examiner* — Karen A. Canella
(74) *Attorney, Agent, or Firm* — Benesch, Friedlander, Coplan & Aronoff LLP

(57) ABSTRACT

Cytotoxic factors having use in modulating cell death, and their use in methods of treating necrosis or apoptosis-related conditions are disclosed. The invention also relates to methods for identifying active agents useful in treating conditions related to cell death. The present inventors have found that different pathogens produce different cytotoxic factor(s) having anticancer activity. The substantially pure cytotoxic factors can be used in a method of treating an infectious disease or a cancer.

6 Claims, 8 Drawing Sheets

Specification includes a Sequence Listing.

(56) References Cited

OTHER PUBLICATIONS

Patera, Carol, ASM News, vol. 66, No. 6 (2000).
Punj, V. et al., Infect. Immun. 68: 4930-4937 (2000).
Punj. V. & Chakrabarty, A. M., Cellular Microbiology, 5(4) pp. 225-231 (2003).
Punj. V. et al., Biochemical and Biophysical Research Communications, vol. 312, pp. 109-114 (2003).
Punj, Vasu et al., Oncogene 2003.
Punj, Vasu et al., Oncogene (2004) 23, 2367-78.
Sznal. Mario et al., The Journal of Clinical Investigation, vol. 105, No. 8, 1027-1030 (2000).
Wu, T. et al., Antimicrobial Agents and Chemotherapy, vol. 44, No. 5, pp. 1200-1208 (May 2000).
Yamada, T. et al., PNAS, vol. 99, No. 22, pp. 14098-14103 (2002).
Yamada, T. et al., Infection & Immunity, vol. 70 No. 12, 7054-62 (2002).
Zaborina, O. et al., Infect. Immun. 67: 5231-5242 (1999).
Zaborina, O. et al., Microbiology 146: 2521-2530 (2000).
Zaborina, O. et al., Molecular Microbiology 31 (5) 1333-1343 (1999).

\* cited by examiner

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial sequence
<220> FEATURE:
<223> OTHER INFORMATION: caspase-3 activity assay reagent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: p-NO2-aniline

<400> SEQUENCE: 1

Asp Glu Val Asp
1

<210> SEQ ID NO 2
<211> LENGTH: 4
<212> TYPE: PRT
<213> ORGANISM: Artificial Sequence
<220> FEATURE:
<223> OTHER INFORMATION: Caspase-9 activity assay reagent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: p-NO2-aniline

<400> SEQUENCE: 2

Leu Glu His Asp
1
```

CYTOTOXIC FACTORS FOR MODULATING CELL DEATH

RELATED APPLICATIONS

The present application is a Continuation and claims the benefit, under 35 U.S.C. § 120, of U.S. patent application Ser. No. 11/485,252, filed Jul. 13, 2006, which is a Continuation of U.S. patent application Ser. No. 10/047,710, filed Jan. 15, 2002, and the benefit, under 35 U.S.C. § 119, of U.S. Provisional Application Ser. No. 60/269,133, filed Feb. 15, 2001, which is expressly incorporated fully herein by reference.

STATEMENT OF GOVERNMENTAL INTEREST

The subject matter of this application has been supported by research grants from the National Institutes of Health (NIH), Bethesda, Md., U.S.A., (Grant Numbers AI 16790-21, ES 04050-16, AI 45541,, CA09432 and N01-CM97567). The government may have certain rights in this invention.

FIELD OF THE INVENTION

The present invention relates to cytotoxic factors secreted by pathogenic microorganisms and inhibitors of cytotoxic factors and their use thereof in modulating cell death by both necrosis and apoptosis. The present invention also relates to methods of producing, isolating and identifying cytotoxic factors useful in modulating apoptosis, and to compositions incorporating substantially pure cytotoxic factors useful in modulating cell death. The invention also relates to methods of treating apoptosis-related conditions. More particularly, the invention relates to the use of a substantially pure cytotoxic factor in a method of inducing apoptosis in a cancer cell and to the use of inhibitors of the cytotoxic factors in a method of treating an infection or other pathogen-induced condition.

BACKGROUND

Infectious diseases can be a product of a number of environmental factors. Underlying any infectious disease is a causative infectious agent. The infectious agent typically is a pathogenic microorganism, for example, a pathogenic bacterium. The degree or ability of a pathogenic microorganism to overcome defense mechanisms and cause a disease is related to its virulence. Pathogenic microorganisms are known to express cytotoxic factors, which allow the pathogen to defend itself from the host immune system and prevent phagocytes (e.g., macrophages and mast cells) from eliminating the pathogen from the body. When the pathogenic microorganisms survive, the microorganisms can invade the host tissues and proliferate, causing severe disease symptoms. Pathogenic bacteria have been identified as a root cause of a variety of debilitating or fatal diseases including, for example, tuberculosis, cholera, whooping cough, plague, and the like. To treat such severe infections, drugs, for example, antibiotics, are administered that either kill the infectious agent or disarm the cytotoxic factors so that the infectious agent is no longer able to defend itself against the host immune system. However, pathogenic bacteria commonly develop resistance to antibiotics and improved agents are needed to prevent the spread of infections due to such microorganisms.

A cancer is a malignant tumor of potentially unlimited growth. It is primarily the pathogenic replication (a loss of normal regulatory control) of various types of cells found in the human body. Initial treatment of the disease is often surgery, radiation treatment or the combination, but locally recurrent and metastatic disease is frequent. Chemotherapeutic treatments for some cancers are available but these seldom induce long term regression. Hence they are not usually curative. Commonly, tumors and their metastases become refractory to chemotherapy, in an event known as the development of multidrug resistance. In many cases, tumors are inherently resistant to some classes of chemotherapeutic agents. In addition, such treatments threaten noncancerous cells, are stressful to the human body, and produce many side effects. Hence, improved agents are needed to prevent the spread of cancer cells. It has been known that many cancers regress when patients are infected with pathogenic bacteria. However, very little is known about how bacterial infections may cause regression of human, cancers.

SUMMARY

The present invention relates to cytotoxic factors that stimulate cell death by necrosis or apoptosis. In one aspect, substantially pure cytotoxic factors have been characterized and isolated. Substantially pure cytotoxic factors are obtained by column, chromatographic fractionation of a growth medium which has been exposed to a pathogenic microorganism. Preferably, the production and secretion of such cytotoxic factors are stimulated during growth of pathogenic organisms in the presence of mammalian proteins.

In another aspect of the present invention, the identification of receptors for mammalian proteins as a means of delineating virulent and avirulent microorganisms can lead to improved specificity for disease treatment.

Yet another aspect of the present invention relates to a method of treating a condition related to cell death resistance or susceptibility comprising the step of administering a cytotoxic factor, an inhibitor of a cytotoxic factor, or a variant or derivative thereof, optionally incorporated in a pharmaceutical carrier.

The cytotoxic factor, or a variant or derivative thereof, can be incorporated into a pharmaceutical composition for use in the prevention and treatment of conditions related to abnormal cell proliferation. For example, a cytotoxic factor can be used to treat a cancer.

An inhibitor of a cytotoxic factor, or a variant or derivative thereof, can be used to treat a bacterial infection by preventing phagocytic cell death and hence allowing the host immune system to combat an invading pathogen.

In another embodiment of the present invention, cytotoxic factors, as well as components of their secretion machinery, can be used as candidates for vaccines against infectious agents.

The present invention also relates to a method of modulating cell death comprising the step of controlling secretion of cytotoxic factors. In a preferred embodiment, the cytotoxic factors can be used as anti-cancer agents against a host of human cancer cells. In addition, cytotoxic factors can be used as targets for drug development through screening or rational design of inhibitors.

These and other aspects, advantages, and features of the invention will become apparent from the following figures and detailed description of the preferred embodiments.

DETAILED DESCRIPTION OF THE PREFERRED EMBODIMENTS

Figure 1:
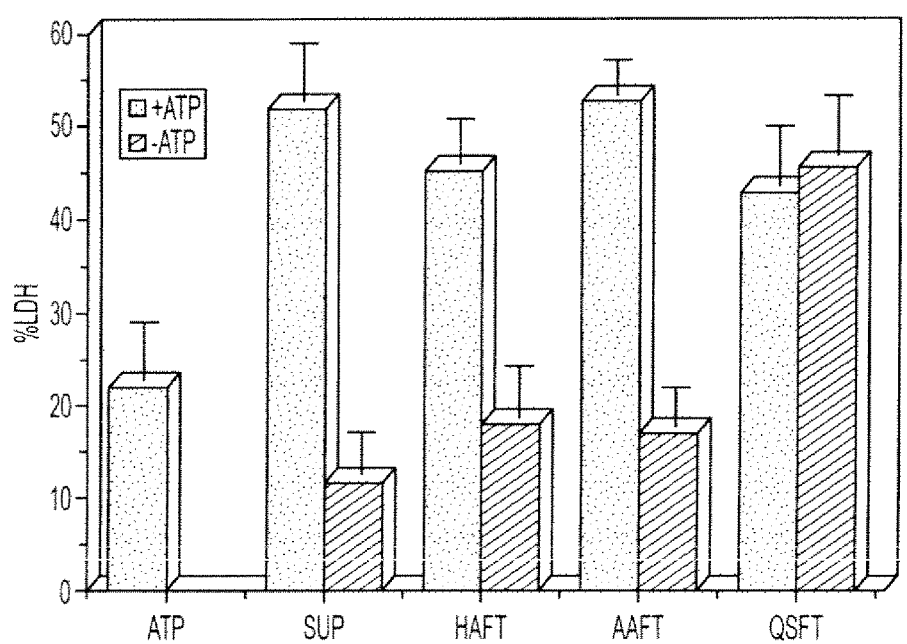
FIG. 1. Chart showing the effect of 1.0 mM ATP on macrophage killing in absence or in presence of the filtered growth, medium supernatant (SUP) or the hydroxyapatite flow through (HAFT). ATP-agarose flow through (AAFT) and Q-sepharose flow through (QSFT) column chromatographic fractions derived from *B. cepacia* growth medium. The extent of macrophage cell death is measured by release of the intracellular enzyme lactate dehydrogenase (LDH). 2 µg of protein from each fraction was used in the assay. All assays were carried out in triplicate and error bars are indicated.

Definitions.

For the purposes of the description herein, the term "cytotoxic factor" refers to a factor secreted by a pathogenic microorganism and which stimulates cell death by necrosis or apoptosis. The term "ATP-dependent", when used to modify the term "cytotoxic factor" refers to a cytotoxic factor which acts to cause cell death in the presence of adenosine 5'-triphosphate (ATP). The term "ATP-independent", when used to modify the term "cytotoxic factor" refers to a cytotoxic factor which acts to cause cell death in the absence of ATP.

For the purposes of the description herein, the term "treatment" includes preventing, lowering, stopping, or reversing the progression or severity of the condition or symptoms being treated. As such, the term "treatment" includes both medical, therapeutic, and/or prophylactic administration, as appropriate.

As used herein, the term "a condition related to resistance to cell death" refers to a disease, state, or ailment characterized by at least a tendency for prolonged cell life when compared with a healthy cell of like kind as determined by a reasonable, skilled physician or clinician. The term "a condition related to cell death susceptibility", as used herein, refers to a disease, state, or ailment characterized by at least a tendency for premature cell death when compared with a healthy cell of like kind as determined by a reasonable, skilled physician or clinician.

The term "substantially pure", when used to modify the term "cytotoxic factor" or "virulence factor", as used herein, refers to a factor isolated from the secreted growth medium in a form substantially free of, or unadulterated by, active inhibitory compounds. The term "substantially pure" refers to a factor in an amount of at least about 75%, by weight, of isolated fraction, or at least "75% substantially pure". More preferably, the term "substantially pure" refers to a compound of at least about 85%, by weight, active compound, or at least "95% substantially pure". The substantially pure cytotoxic factor or virulence factor can be used in combination with one or more other substantially pure compounds or isolated cytotoxic factors.

As used herein, the term "a variant or derivative thereof" refers to a compound or substance obtained by chemical modification or manipulation of genes encoding the compound or substance. When referring to a variant or derivative of a cytotoxic factor, the variant or derivative can be obtained by chemical modification of the cytotoxic factor, or by manipulation of genes encoding such cytotoxic factors, for example by altering the basic composition or characteristics of the cytotoxic factor, but not its toxicity. Similarly, a derivative of an inhibitor of a cytotoxic factor can include chemical modifications to the chemical structure of the inhibitor or manipulation of genes encoding the inhibitor. For example, the antibiotic penicillin can be chemically modified to provide derivatives that are more potent or have a wider spectrum than penicillin itself.

A "therapeutically effective amount" is an amount effective to prevent development of, or to alleviate the existing symptoms of, the subject being treated. Determination of a therapeutically effective amount is well within the capability of those skilled in the art.

General.

The present invention provides cytotoxic (or virulence) factors that are secreted by pathogenic microorganisms and that stimulate cell death by necrosis or apoptosis. When pathogenic microorganisms invade human or animal tissues, phagocytic cells are a first line of defense in the host immune system. Typically, phagocytes seek out and destroy foreign pathogens invading the body. However, cytotoxic factors secreted by microbial pathogens can stimulate cell death in the phagocytic cells. Thus, the phagocytes are prevented from performing their protective immune function.

The inventors have previously reported that many pathogenic bacteria secrete ATP-dependent cytotoxic factors, for example ATP-utilizing enzymes, that cause phagocytic cell death by necrosis. [Zaborina O. et al., Infect. Immun. 67: 5231-5242 (1999); Melnikov A. et al, Mol. Microbiol. 36: 1481-1493 (2000); and Punj et al. *Infect. Immun.* 68: 4930-4937 (2000).] ATP-utilizing enzymes act on various energy-related nucleotide derivatives such as ATP, adenosine 5'-diphosphate (ADP), adenosine 5'-monophosphate (AMP), or adenosine, converting them to various products that in turn can modulate the death of phagocytic cells such as macrophages and mast cells through activation of purinergic receptors.

One aspect of the present invention relates to the discovery that ATP-independent cytotoxic factors, for example redox proteins, are also secreted by some species of pathogenic microorganisms, and that such factors cause phagocytic cell death by apoptosis. [see Zaborina O. et al. *Microbiology* 146: 2521-2530 (2000).]

Another aspect of the present invention relates to the surprising discovery that ATP-Independent cytotoxic factors induce apoptosis in cancer cells. Normally cancer cells are not susceptible to apoptotic death. It is known that mammalian cell apoptosis requires the presence of p53 protein. However, in 50% of human cancers, inactivating mutations in the gene encoding the p53 tumor suppressor protein are present. Although it is also known that p53 regulates the expression of redox proteins in mammalian cells, mammalian redox proteins have not been directly implicated in cancer cell apoptosis. Neither has the role of microbial ATP-independent cytotoxic factors in inducing apoptosis in cancer cells or in reducing tumor size been shown. Thus, such cytotoxic factors may be used to treat a condition related to resistance to cell death. Such conditions may include, for example, human melanoma, leukemia, breast cancer, ovarian cancer, lung cancer, mesenchymal cancer, colon cancer and aerodigestive tract cancers (e.g. stomach, esophagus, larynx and oral cancers).

Another aspect of the present invention relates to methods of identification and characterization of cytotoxic factors secreted by pathogenic microorganisms. Such methods can provide a means for discovering appropriate inhibitors or stimulators of cell death. Inhibitors and stimulators can be developed as pharmaceutical drugs and used to treat conditions characterized by resistance or susceptibility to cell death.

Another aspect of the invention relates to cytotoxic factors that have been characterized and isolated and to inhibitors of such cytotoxic factors. The cytotoxic factors can be activated or inactivated in accordance with a method of the invention to prevent or treat a condition related to cell death. An inhibitor of a cytotoxic factor can be used to treat a condition related to cell death susceptibility.

Secretion of Cytotoxic Factors.

In one aspect of the present invention, cytotoxic factors of the present invention are secreted by a number of different pathogenic microorganisms, including bacteria and protozoa. Examples of pathogenic bacteria suitable for providing the cytotoxic factors include, but are not limited to, *Pseudomonas aeruginosa, Burkholderia cepacia, Vibrio cholerae*, and *Mycobacterium bovis*. In addition, cytotoxic factors are secreted by pathogens, such as *Leishmania amazonemis* and *Brugia malayi*.

*P. aeruginosa*, an opportunistic pathogen, *B. cepacia*, which causes fatal infections in patients suffering from cystic fibrosis and chronic granulomatous disease, *Vibrio cholerae*, the intestinal pathogen that causes cholera and the slow-growing virulent group of mycobacteria, such as *M. tuberculosis* or *M. bovis*, that cause tuberculosis have been found to secrete ATP-utilizing enzymes.

In addition to secreting ATP-utilizing enzymes, the inventors have found that *P. aeruginosa* secretes ATP-independent cytotoxic factors. These have been identified as two redox proteins, azurin and cytochrome $c_{551}$. *B. cepacia* has also been shown to secrete the redox proteins. *M. bovis* has been shown to also secrete cytotoxic factors having high ATP-independent cytotoxicity towards phagocytic cells.

Stimulation of the Secretion of Cytotoxic Factors in the Presence of Mammalian Proteins.

In another aspect of the present invention, production and secretion of cytotoxic factors are stimulated during growth of pathogenic organisms in the presence of mammalian proteins. For example, the secretion of cytotoxic factors by pathogenic microorganisms such as *P. aeruginosa, M. bovis* and *B. cepacia* is stimulated by the presence of mammalian proteins such as kappa-casein, bovine serum albumin, ovalbumin or α2-macroglobulin. It is suggested, but not relied upon herein, that the pathogenic microorganisms sense the presence of certain mammalian proteins as indicative of the mammalian host environment, thereby opening up the secretion machinery for the cytotoxic agents to counter and subvert host defense.

The inventors have determined that several clinical (virulent) isolates of *B. cepacia* secrete large amounts of ATP-utilizing enzymes such as adenylate kinase or 5'-nucleotidase, while several environmental (avirulent) isolates secreted only reduced amounts of these enzymes, in clinical isolates, such as *B. cepacia* strain 38, the level of secretion of cytotoxic factor is greatly enhanced in the presence of α2-macroglobulin in the growth medium. The secreted products from clinical isolates have a higher level of cytotoxicity towards macrophages and mast cells than that from environmental isolates. The clinical isolates that demonstrate enhanced secretion of cytotoxic factors in the presence of α2-macroglobulin also demonstrate the presence of the receptors for α2-macroglobulin on their surface.

In a preferred embodiment of the present invention, the production and secretion, of ATP-independent cytotoxic factors are stimulated during growth of pathogenic organisms in the presence of mammalian proteins.

Hence, increased secretion of cytotoxic factors can be obtained by growing pathogenic organisms in growth media containing mammalian proteins. Suitable growth media are, for example, L broth, nutrient broth, Trypticase soy broth and tryptone-yeast extract both (Difco Laboratories, Maryland, U.S.A.). Typically, approximately 500 ml to 1,000 ml of sterile autoclaved growth medium are inoculated with between about $10^4$ to $10^6$ cells/ml. The inoculated medium is then incubated under conditions suitable to allow growth of the microorganism, usually on a rotary shaker at 30° C.

to 37° C. Selection of growth media, incubation conditions, and other factors allowing successful culture of bacteria and other microorganisms will be clearly apparent to one skilled in the art. The inventors have observed that maximum concentrations of cytotoxic factors in the growth medium occur late in the exponential growth phase and early in the stationary growth phase.

In another embodiment of the present invention, the identification of receptors for mammalian proteins provides a means of delineating virulent and avirulent strains of microorganisms. For example, the presence of the receptors for α2-macroglobulin primarily in clinical isolates, but not in environmental isolates, not only correlates with the ability of the former to secrete cytotoxic agents as weapons against the host defense, but also allows delineation between the clinical, virulent strains with the environmental, avirulent strains. Hence, virulent strains of organisms can be identified and then tested for their antibiotic sensitivity or for other clinical purposes.

Purification of ATP-Independent Cytotoxic Factors.

In another aspect of the present invention, substantially pure ATP-independent cytotoxic factors are obtained by column chromatographic fractionation of the growth medium of the secreting microorganism. Preferably, the bacterial cells are removed from the growth medium prior to fractionation. This may be achieved by initial centrifugation and subsequent filtering the growth medium. Suitable filters are typically less than or equal to about 0.5 μm pore size and preferably about 0.2 μm. However, other methods of pathogen removal will be known to those skilled in the art.

Unfractionated growth media do not have high ATP-independent cytotoxic activity and hence column chromatographic fractionation is necessary to enhance apoptosis-inducing activity. Fractionation removes ATP-dependent cytotoxic factors, ft is also suggested, but not relied upon herein, that fractionation also removes inhibitors of ATP-independent cytotoxic factors that may be present in the unfractionated growth medium.

Chromatographic techniques useful in purifying cytotoxic factors will be known to those skilled in the art. These include, for example, ion-exchange chromatography, hydroxyapatite chromatography, affinity chromatography, and gel-filtration chromatography. Chromatographic columns useful in the fractionation of bacterial growth media include, for example: Hydroxyapatite; Superdex 75 or 200; Superose 6 or 12; Sephacryl S; Sephadex G or Sephadex LH; Mono Q or Mono S; Q-Sepharose; DEAE Sepharose or CM Sepharose; Sepharose XL; ATP-Sepharose; Hi Trap Blue; Blue Sepharose; DNA Cellulose or Sepharose 2B, 4B or 6B, available from Amersham Pharmacia Biotech AB, Uppsala, Sweden or Bio-Rad Laboratories, Hercules, Calif., U.S.A.

Preferably, ATP-utilizing enzymes are isolated by column chromatographic fractionation as flow-through or eluted fractions of hydroxyapatite and ATP-agarose columns. During such fractionation, the ATP-utilizing enzymes, such as ATPase or adenylate kinase are adsorbed on the column and can be removed or purified further. (See, for example, Markaryan et al., J. Bacteriol., 183, pp 3345-3352, 2001.)

In a preferred embodiment of the present invention, ATP-independent cytotoxic factors are isolated as flow-through fractions of Q-sepharose columns (QSFT). Q-sepharose is a quaternary ammonium strong anion exchanger. Such columns can be obtained from Amersham Pharmacia Biotech AB, Uppsala, Sweden. The supernatant (SUP) or other column fractions such as hydroxyapatite column flow through fraction (HAFT) or ATP-agarose column flow through fraction (AAFT) do not normally show high ATP-independent cytotoxicity.

Characterization of ATP-Independent Cytotoxic Factors.

In a further aspect of the present invention, fractionated growth media are tested to determine the presence of ATP-independent cytotoxic factors. The extent of cell death may be measured by the release of the intracellular enzyme lactate dehydrogenase (LDH) as described in Zaborina et al., Infection and Immunity. 67, 5231-5242 (1999) and Zaborina et al. Microbiology, 146, 2521-2530 (2000).

The ability of ATP-independent cytotoxic factors to induce apoptosis may be observed by mitosensor ApoAlert confocal microscopy using a MITOSENSOR™ APOLER™ Mitochondrial Membrane Sensor kit (Clontech Laboratories, Inc., Palo Alto, Calif., U.S.A.). In the assay, healthy, non-apoptotic cells fluoresce red while apoptotically dead cells fluoresce green. A combination of red and green produces yellow fluorescing cells that represent apoptotically dying cells. See Zaborina et al. Microbiology, 146, 2521-2530 (2000).

Apoptosis is mediated via activation of a cascade of enzymes known as caspases, which are cysteine proteases cleaving at aspartic residues. Hence, apoptosis may also be detected by measuring two important caspase activities, namely that of caspase 9 and caspase-3, which are known to be activated during apoptosis by the oligomerization of the cytochrome c released from mitochondria with a cytosolic protein Apaf-1, using the method described in Zou et al., J. Biol. Chem., 274: 11549-11556 (1999).

In addition, apoptosis may be observed by detecting apoptosis-induced nuclear DNA fragmentation using the APOLERT DNA fragmentation kit (Clontech Laboratories, Inc., Palo Alto, Calif., U.S.A.). This assay is based on terminal deoxynuclotidykransferase (Tdt)—mediated dUTP nick-end labeling (TUNEL), where Tdt catalyzes the incorporation of fluorescein-dUTP at the free 3'-hydroxyl ends of fragmented DNA in cells undergoing apoptosis. The incorporation of fluorescein-dUTP in the fragmented nuclear DNA generates green fluorescence which is detected by confocal microscopy.

In a preferred embodiment of the present invention, fractionated growth media are tested to determine the ability of such fractions to induce apoptosis. Such methods are useful in the identification and characterization of ATP-independent cytotoxic factors.

Identification of ATP-Independent Cytotoxic Factors.

In another aspect, this invention provides characterized cytotoxic factors exhibiting ATP-independent apoptosis-triggering cytotoxicity. The inventors have found that the QSFT fraction of *P. aeruginosa* and *B. cepacia* is enriched with two proteins, azurin and cytochrome $c_{551}$. The identification of these two proteins is based on their separation on SDS-PAGE and identification of their N-terminal amino acid sequences. In contrast, SDS-PAGE analysis of the *M. bovis* QSFT fraction shows a thick 65 kDa band of bovine serum albumin (BSA), which is a constituent of the 7119 medium used for growing *M. bovis*, as well as several bands of greater than 45 kDa molecular mass, but not the bands characteristic of cytochrome $c_{551}$ or azurin. (See Example 9.)

Azurin and/or cytochrome $c_{551}$ and the QSFT fractions exhibit apoptosis-triggering cytotoxicity towards phagocytic cells. A purified azurin; cytochrome $c_{551}$ mixture, or the *B. cepacia* QSFT fraction, treated with a mixture of anti-azurin and anti-cytochrome $c_{551}$ antibodies, show greatly diminished macrophage cytotoxicity. In contrast, the *M. bovis*

QSFT fraction, when pretreated with anti-azurin/anti-cytochrome $c_{551}$ antibodies, shows very little reduction in cytotoxicity, confirming that *M. bovis* QSFT fraction contains cytotoxic factors other than azurin or cytochrome $c_{551}$. Thus different pathogens secrete different apoptosis-inducing cytotoxic factors, all of which would be excellent targets for anti-infective drug development.

Induction of Apoptosis in Cancer Cells by ATP-Independent Cytotoxic Factors.

The present invention provides methods of using ATP-independent cytotoxic factors to induce apoptotic cell death in cancer cells. ATP-independent cytotoxic factors, such as azurin and cytochrome $c_{551}$, can be used to treat conditions related to an abnormal failure of cell death. It is well known that cancer cells are not prone to undergoing apoptosis. In accordance with one aspect of the present invention, administering a cytotoxic factor or active agent stimulating cytotoxic factor secretion in an amount sufficient to induce cancer cell apoptosis would be beneficial in reducing tumor size in vivo and retarding the growth of tumors. For example. Tests comparing azurin and cytochrome $c_{551}$ to a known anti-melanoma cancer drug [5-(3,3'-N,N'-dimethyl triazen-1-yl)-imidazole-4-carhoxyamide] (DTIC) show that a mixture of azurin and cytochrome $C_{551}$ provides a potent, non-toxic composition that promotes tumor regression in vivo in nude mice.

Use of Cytotoxic Factors in the Treatment of Infectious Disease.

In another aspect of the present invention, characterization of cytotoxic factors can be useful for identifying new substances that inhibit cell death, for example, in an infectious disease. For example, inhibition of the secretion or activity of an ATP-utilizing cytotoxic factors, or the production of ATP, can reduce or eliminate cytotoxic activity by a disease-causing pathogen.

Accordingly, appropriately administering a compound that inhibits the secretion or activity of cytotoxic factors provides a useful tool for anti-infective development. Examples of active agents useful for inhibiting activity of cell death inducing cytotoxic factor can include antibodies for cytotoxic factors, as well as analogues of ATP that prevent the activation of ATP-utilizing enzymes. Examples of cytotoxic factors and active agents for inhibiting or stimulating cytotoxic factor secretion or expression include, but are not limited to, ATP-utilizing enzymes, redox proteins, activators of ATP-production, inhibitors of ATP production, activators of redox proteins, and inhibitors of redox proteins.

Administration of Pharmaceutical Compositions Comprising Cytotoxic Factors.

Pharmaceutical compositions comprising cytotoxic factors can be manufactured in any conventional manner, e.g. by conventional mixing, dissolving, granulating, dragee-making, emulsifying, encapsulating, entrapping, or lyophilizing processes. The substantially pure cytotoxic factor or other agent can be readily combined with a pharmaceutically acceptable carrier well-known in the art. Such carriers enable the preparation to be formulated as a tablet, pill, dragee, capsule, liquid, gel, syrup, slurry, suspension, and the like. Suitable excipients can also Include, for example, fillers and cellulose preparations. Other excipients can include, for example, flavoring agents, coloring agents, detackifiers, thickeners, and other acceptable additives, adjuvants, or binders.

The compositions of the invention can be used in treatment of a condition related to cell death or in the prevention thereof. The substantially pure cytotoxic factor can be administered in an amount sufficient to stimulate the natural response of the host immune system and the secretion machinery of the host organism, for example as a vaccine. Typically, the host organism is a mammal, such as a human or animal.

The composition can be administered by any suitable route, for example, by oral, buccal, inhalation, sublingual, rectal, vaginal, transurethral, nasal, topical, percutaneous, i.e., transdermal or parenteral (including intravenous, intramuscular, subcutaneous and intracoronary) administration. The compositions and pharmaceutical formulations thereof can be administered in any amount effective to achieve its intended purpose. More specifically, the composition is administered in a therapeutically effective amount.

The exact formulation, route of administration, and dosage is determined by the attending physician in view of the patient's condition. Dosage amount and interval can be adjusted individually to provide plasma levels of the active cytotoxic factor which are sufficient to maintain therapeutic effect. Generally, the desired cytotoxic factor is administered in an admixture with a pharmaceutical carrier selected with regard to the intended route of administration and standard pharmaceutical practice. Pharmaceutical compositions used in accordance with the present invention can be formulated in a conventional manner using one or more physiologically acceptable carriers comprising excipients and auxiliaries that facilitate processing of the cytotoxic factor, active agents, for inhibiting or stimulating the secretion of cytotoxic factors, or a mixture thereof into preparations which can be used therapeutically.

Stimulation and Inhibition of the Secretion of Cytotoxic Factors.

The identification and characterization of the cytotoxic factors also can lead to the development of methods of stimulating of cytotoxic factor secretion. Pathogenic organisms have been shown to secrete large amounts of cytotoxic factors in the presence of mammalian proteins. This principle can be modified in the human body to provide new methods of stimulating desired, or inhibiting undesired, cytotoxic factor production. Such methods are useful for inhibiting or stimulating cell apoptosis. The understanding of the cytotoxic factors, and the characterization and development thereof, also allows for drug development and screening of active agents or compounds suitable for modulating the cytotoxic factor activity or secretion. The understanding of the secretion machinery related to cytotoxic factor secretion in cells additionally provides new avenues of developing and identifying the design of useful inhibitors or stimulators of cytotoxic factors. The delineation and identification of the presence of receptors for mammalian proteins also can be used as a means to differentiate between the virulent and avirulent microorganisms, which can provide specificity in treating the disease. Components of the secretion machinery, as well as cytotoxic factors themselves, can be used as vaccines.

Modification of Cytotoxic Factors.

Cytotoxic factors also can be chemically modified or genetically altered to produce variants that lack an ATP-utilizing enzyme or redox activity, but retain toxicity. Mutations and/or truncations of the gene can produce cytotoxic agents of varying compositions also demonstrating functional activity. In particular, truncated derivatives with high efficacy and low antigenicity can be produced from the original cytotoxic factor. Such modified or altered cytotoxic factors, and such cytotoxic agents, also are included in the scope of the present invention.

A more complete understanding of the present invention can be obtained by reference to the following specific Examples. The Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations. Modifications and variations of the invention as hereinbefore set forth can be made without departing from the spirit and scope thereof, and, therefore, only such limitations should be imposed as are indicated by the appended claims.

EXAMPLES

Example 1

Stimulation of the Secretion of Cytotoxic Factors by Mammalian Proteins

Clinical and environmental isolates (five of each) of *B. cepacia* were grown in proteose peptone-yeast extract (PPY) broth with and without added α2-macroglobulin (1 mg/ml). After growth for 10 hours at 34° C. on a shaker, a portion of the growth medium from each culture was centrifuged and the supernatant filtered through a 0.22 µm millipore filter to remove whole cells and debri. The filtered supernatant was then tested for adenylate kinase activity as described in Melnikov A. et al., Mol. Microbiol., 36: 1481-1493 (2000). Adenylate kinase transfers the terminal phosphate from $[_\gamma$-$^{32}$P]ATP to AMP giving rise to ADP. The products of this reaction were then detected by thin-layer chromatography. Secretion of adenylate kinase was minimal when *B. cepacia* cells were grown in PPY broth. However, secretion from the clinical isolates, but not for the environmental isolates, was stimulated in the presence of α2-macroglobulin.

Immunofluorescence microscopy with anti-α2-macroglobulin antibody showed that the clinical isolates had receptors that bound α2-macroglobulin while the environmental isolates lacked such receptors. The clinical and environmental isolates of *B. cepacia* were grown in absence or in presence of 1 mg/ml α2-macroglobulin in PPY broth for 1 hr. Extraneous α2-macroglobulin was removed by washing with phosphate-buffered saline. The cells were incubated for 2 hours with fluorescein isothiocyanate (FITC)-conjugated α2-macroglobulin antibodies, obtained by injecting rabbits with α2-macroglobulin. After washing with phosphate-buffered saline, the FITC conjugated antibody treated cells were fixed in 16% paraformaldehyde, coated on poly-L-lysine coated slides, and examined by confocal microscopy. Only the clinical isolates that showed enhanced cytotoxic factor secretion in the presence of α2-macroglobulin fluoresced (green fluorescing cells), demonstrating the presence of the receptors for α2-macroglobulin.

Example 2

ATP-dependent Macrophage Killing by Filtered Supernatant or Column Chromatographic Fractions Derived from *B. cepacia* Growth Medium A clinical strain of *B. cepacia* (strain 38—collection number 95828. D. G. Allison, University of Manchester Institute of Science and Technology, Manchester, UK) was grown in TB broth (10 g of Bacto tryptone, 3 g of Bacto beef extract per liter of water) at 34° C. on a shaker to an $OD_{550nm}$ of 1.3. The growth medium was then centrifuged and the supernatant filtered through a 0.22 µm millipore filter to remove whole cells and debri. Macrophage cells were isolated from J774 cell lines and grown in RPMI medium 1640 (GIBRO-BRL, Grand Island, N.Y.) as described by Zaborina O. et al, Infect. Immun. 61: 5231-5242 (1999). The filtered growth medium was added to hydroxyapatite, ATP-agarose, and Q-sepharose columns in sequence. The flow-through fraction from the hydroxyapatite column (HAFT) was fractionated on the ATP-agarose column (AAFT). The AAFT fraction was then fractionated on the Q-sepharose column (QSFT).

$10^6$ macrophages were added to wells in a 96 well plate and incubated for two hours in a $CO_2$ incubator for attachment. 2 µg of protein from the supernatant or the flow-through fraction from each of the above columns was added to the wells and the plates incubated for 4 hrs in the presence or absence of 1.0 mM ATP. The extent of macrophage cell death was then measured by the release of the intracellular enzyme lactate dehydrogenase (LDH) as described by Zaborina O. et al. Infect. Immun., 67: 5231-5242 (1999). The extent of macrophage killing, in the presence and in the absence of 1.0 mM ATP, by the filtered supernatant (SUP) and the HAFT, AAFT and QSFT column fractions is shown in FIG. 1. All assays were carried out in triplicate and error bars are indicated.

Example 3

Figure 2:
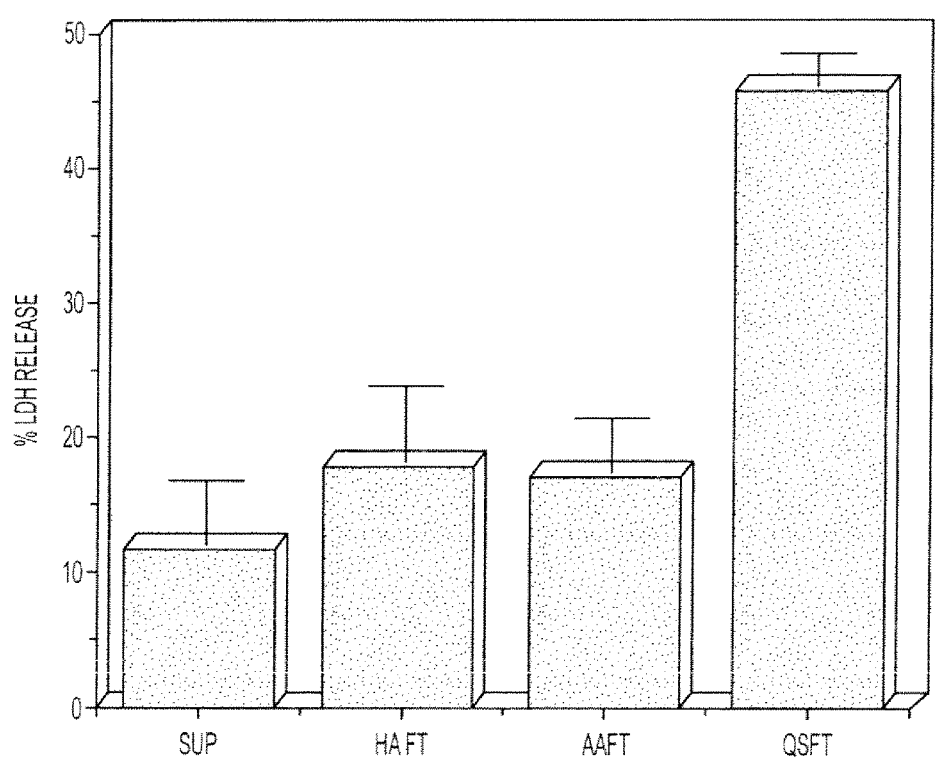
FIG. 2. Chart showing the effect of filtered growth medium supernatant (SUP) and column chromatographic fractions (HAFT, AAFT and QSFT) of *B. cepacia* on macrophage cell death in the absence of ATP. The extent of macrophage cell death is measured by the release of the intracellular enzyme lactate dehydrogenase (LDH). All assays were carried out in triplicate and error bars are indicated.
Figure 3A:
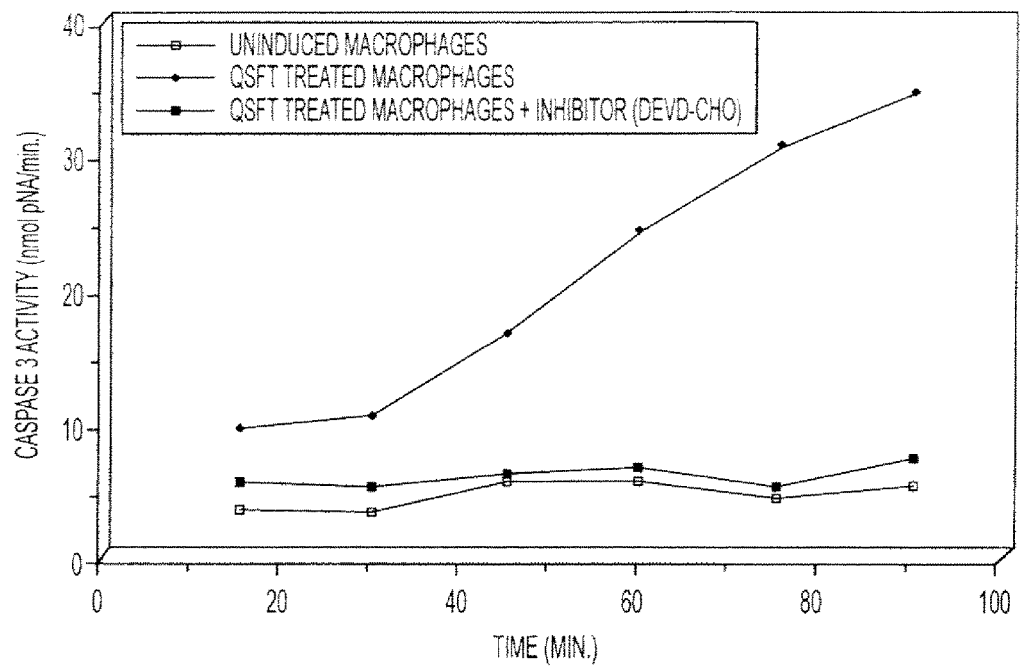
FIG. 3. Graphs showing caspase activities (FIG. 3A-caspase-3.
FIG. 3B-caspase-9) in the cytosolic extracts of J774 macrophages treated with *B. cepacia* QSFT fraction. Cytosolic extracts were prepared from macrophages incubated overnight with *B. cepacia* QSFT traction (10 µg protein) and from untreated macrophages. The substrate for the determination of caspase-3 activity was Ac-DEVD-pNA (N-acetyl-Asp-Glu-Val-Asp-p-NO$_2$-aniline (SEQ ID NO: 1)). The substrate for caspase-9 activity was Ac-LEHD-pNA (N-acetyl-Leu-Glu-His-Asp-p-NO$_2$-aniline (SEQ ID NO: 2)). Extracts were incubated with the substrate at 37° C. for the times indicated. 10 µg of macrophage cytosolic protein was used in each case. Release of pNA (p-nitroaniline) was determined spectrophotometrically at 405 nm.
Figure 3B:
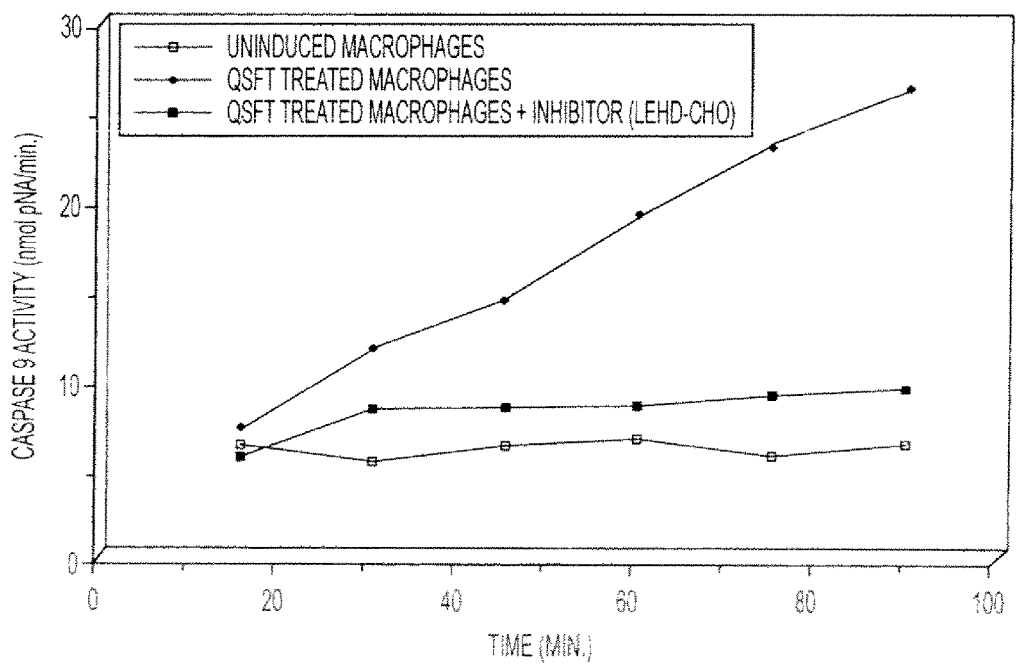
Figure 4:
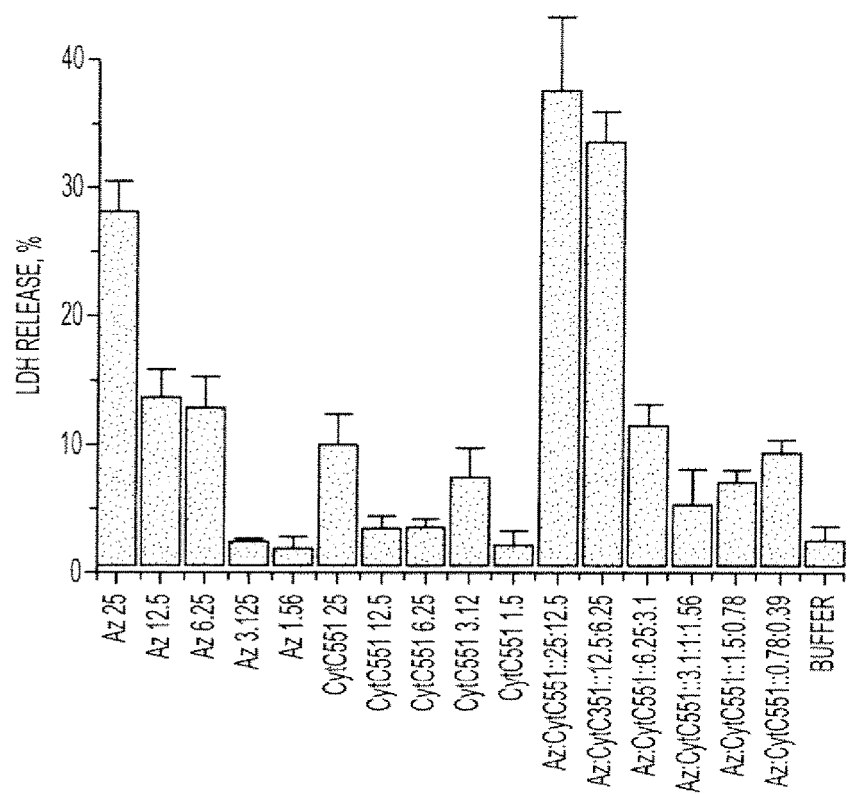
FIG. 4. Chart showing cytotoxicity, as measured by % lactate dehydrogenase (LDH) release, in macrophages in presence of azurin (Az), cytochrome $c_{551}$ (Cyt $C_{551}$) and combination thereof. The numbers represent µg protein. The buffer control (buffer) is shown at right.
Figure 5A:
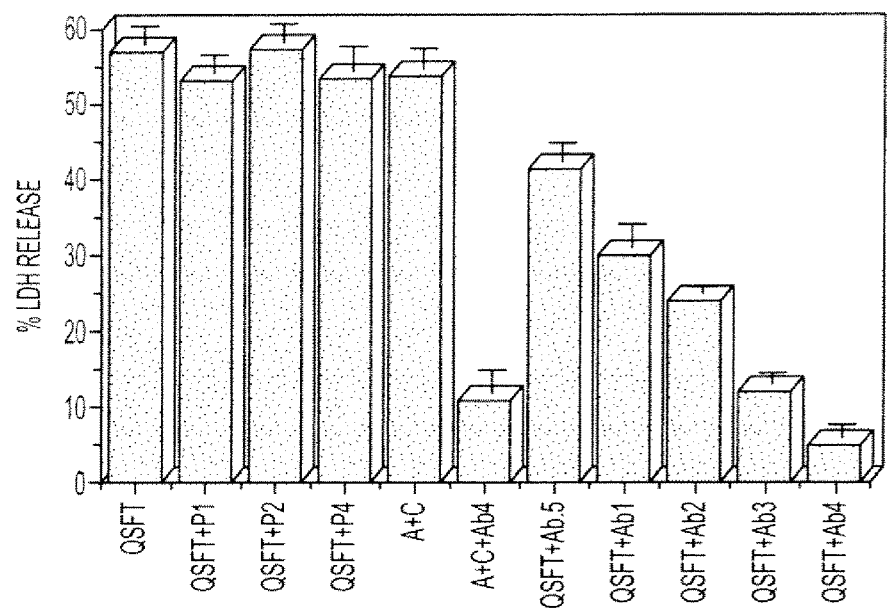
FIG. 5. Chart showing the effects of anti-azurin and anti-cytochrome c551 antibodies on cytotoxicity of *B. cepacia* (A) and *M. bovis* (B) QSFT fractions and in the presence of preimmune serum. A, azurin (50 µg); C, cytochrome c551 (25 µg); ab, combination of anti-azurin and anti-cytochrome c551 antibodies; P, preimmune serum. 2 µg of QSFT fraction were used in each assay. The numbers after ab and P represent µg of the antibody or preimmune protein. Results shown are means±standard deviations of triplicate experiments.
Figure 5B:
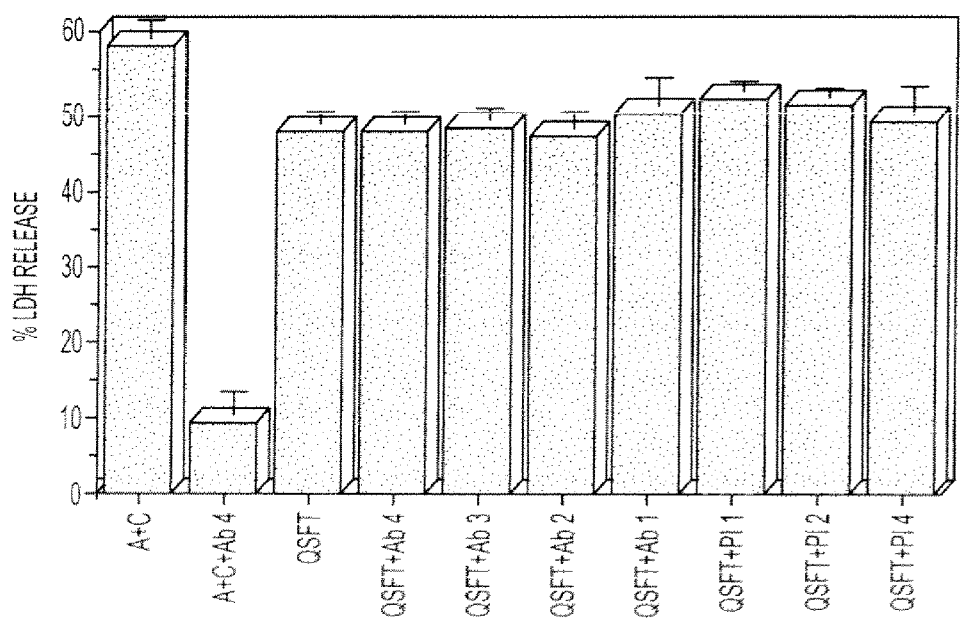

ATP-independent Macrophage Killing by Filtered Supernatant or Column Chromatographic Fractions Derived from *B. cepacia* Growth Medium The supernatant (SUP) and column chromatographic fractions (HAFT, AAFT and QSFT) of *B. cepacia* growth medium were as in Example 2. Macrophage isolation was as in Example 2. The extent of macrophage cell death has been determined by release of LDH as in Example 2 and is shown in FIG. 2. Only the QSFT traction shows high ATP-independent cytotoxicity towards macrophages.

Example 4

Induction of Apoptosis in Macrophages by *P. aeruginosa* Cytotoxic Factor

*P. aeruginosa* was grown in L broth at 37° C. for 12 hours to an $OD_{550nm}$ of 1.2. The growth medium was then centrifuged and the supernatant filtered through a 0.22 µm filter. Supernatant (SUP) and column chromatographic fractions (HAFT, AAFT and QSFT) were collected as in Example 2. Macrophage isolation was as in Example 2. 2 µg of protein from the supernatant or one of the flow-through fractions was added to $1\times10^5$ macrophages in 200 µl of RPMI medium and the mixture incubated overnight. Induction of apoptosis in macrophages either untreated or treated by overnight incubation with the SUP or the HAFT, AAFT or QSFT fractions was measured by confocal microscopy using the ApoAlert Mitochondria Membrane Sensor kit (Clontech Laboratories, Inc., Palo Alto, Calif., U.S.A.) as described by Zaborina O. et al., *Microbiology* 146: 2521-2530 (2000).

In this assay, healthy, non-apoptotic cells fluoresce red while apoptotically dead cells fluoresce green. A combination of red and green produces yellow fluorescing cells, indicating apoptotically dying cells. Nontreated macrophages or macrophages treated overnight with the SUP, HAFT or AAFT fractions fluoresced primarily red, indicating a lack of apoptotic cell death. Macrophages treated overnight with the QSFT fraction fluoresced mostly green, indicating the apoptotic death of most of the macrophages. A time course study showed that apoptosis set in at about 6 hours (indicated by a combination of red and green fluorescence making the cell yellow) and was complete in 12 to 16 hours.

Example 5

Induction of Apoptosis in Mast Cells by *B. cepacia* Cytotoxic Factors

Mast, cells were isolated by the method described by Melnikov A. et al., Mol, Microbiol 36: 1481-1493 (2000). *B. cepacia* fractionated growth medium was prepared as in Example 2. Induction of apoptosis in mast cells by *B. cepacia* cytotoxic factor was determined using confocal microscopy, as described in Example 4.

Nontreated mast cells or mast cells, treated overnight with the SUP, HAFT or AAFT fractions of *B. cepacia* growth medium, fluoresced primarily red, indicating a lack of apoptotic cell death. Mast cells treated overnight with the QSFT fraction of *B. cepacia* growth medium fluoresced mostly green, indicating the apoptotic death of most of the mast cells.

Example 6

Induction of Apoptosis in Macrophages by *B. cepacia* and *M. bovis* QSFT Fractions Macrophage isolation was as in Example 2. Induction of apoptosis in macrophages by *B. cepacia* and *M. bovis* cytotoxic factors was determined using the methods of Example 4. Induction of apoptosis of macrophages was observed when they were treated with the *B. cepacia* and *M. bovis* QSFT fractions.

Example 7

Measurement of Caspase Activities (caspase-3 and caspase-9) in the Cytosolic Extracts of Macrophages Treated with the *B. cepacia* QSFT Fraction Macrophage isolation was as in Example 2. Macrophages are treated overnight with the *B. cepacia* QSFT fraction using the method described in Example 2. The preparation of macrophage cytoslic extract and the caspase assays were as described by Zaborina O. et al., Microbiology 146: 2521-2530 (2000).

Briefly, determination of caspase-3 activity was performed using Ac-DEVD-pNA (N-acetyl-Asp-Glu-Val-Asp-p-$NO_2$-aniline) as a substrate. Release of pNA (p-nitroaniline) was determined spectrophotometrically at 405 nm from the caspase-3 substrate (200 μm) after 15, 30, 45, 60, 75 and 90 min incubation at 37° C. (FIG. 3A) with uninduced macrophage cytosolic extract; cytosolic extract of macrophages incubated, overnight with the *B. cepacia* QSFT fraction (10 μg protein); and cytosolic extract of macrophages incubated overnight with the B cepacia QSFT fraction (10 μg protein) and added inhibitor (DEVD-CHO). 10 μg of macrophage cytosolic protein was used in each case.

In the caspase-9 assay, release of pNA from 200 μM of the caspase-9 substrate Ac-LEHD-pNA (N-acetyl-Leu-Glu-His-Asp-p-$NO_2$-aniline) was determined, after 15, 30, 45, 60, 75 and 90 min incubation (FIG. 3B), with uninduced macrophage cytosolic extract, cytosolic extract of macrophages incubated overnight with the *B. cepacia* QSFT fraction (10 μg protein) and cytosolic extract of macrophages incubated overnight with the *B. cepacia* QSFT fraction (10 μg protein) plus inhibitor (LEHD-CHO). 10 μg of macrophage cytosolic protein was used in each case.

DEVD-CHO and LEHD-CHO respectively block Caspase 3 and Caspase 9 activity and are available from Biomol Research Laboratories, Plymouth Meeting, Pa., U.S.A. The activities of both caspase-9 and caspase-3 increased when macrophages were treated overnight with the *B. cepacia* QSFT fraction (FIGS. 3A and B). These activities remained very low for untreated macrophages or with inhibitor present, suggesting that the induction of apoptosis by the QSFT fractions involves caspase activation.

Example 8

TUNEL Assay to Measure Nuclear DNA Fragmentation in Macrophages Treated with *M. bovis* or *B. cepacia* QSFT Fractions Fractionated *B. cepacia* growth medium was obtained using the method described in Example 2. *M. bovis* BCG was grown in Middlebrook 7H9 broth (Difco Laboratories, Maryland, U.S.A.) supplemented with 2% glycerol, 0.02% TWEEN®80 and ADC (ablumin/dextrose/citrate) (available from Difco Laboratories, Maryland, U.S.A.). The bacteria were grown for several days at 32° C. on a shaker before harvesting. Fractionated *M. bovis* growth medium was obtained using the method described in Example 2. Macrophage isolation was as in Example 2. Induction of apoptosis in macrophages either untreated or treated by overnight incubation of the SLIP or the HAFT, AAFT or QSFT fractions was measured using confocal microscopy by detecting apoptosis-induced nuclear DNA fragmentation with the ApoAlert DNA fragmentation kit (Clontech Laboratories, Inc., Palo Alto, Calif., U.S.A.). This assay is based on terminal deoxynuclotidyltransferase (Tdt)—mediated dUTP nick-end labeling (TUNEL), where Tdt catalyzes the incorporation of fluorescein-dUTP at the free 3'-hydroxyl ends of fragmented DNA in cells undergoing apoptosis. The incorporation of fluorescein-dUTP in the fragmented nuclear DNA generates green fluorescence which is detected by confocal microscopy.

Macrophages treated with either the *M. bovis* or *B. cepacia* QSFT fractions showed a yellow-green nucleus in the red cytoplasmic background, indicating nuclear DNA fragmentation. Little or no fragmentation was observed with untreated macrophages or with macrophages treated with other column fractions.

Example 9

SDS-PAGE Analysis of Proteins in the Supernatant and the AAFT, HAFT and QSFT Fractions of Growth Media from *P. aeruginosa, B. cepacia* and *M. bovis*

SDS-PAGE separation showed the proteins present in the supernatant and the AAFT, HAFT and QSFT Fractions of *P. aeruginosa, B. cepacia* and *M. bovis*. The QSFT medium traction from mucoid *P. aeruginosa* strain 8821 showed the presence of two bands, a 18 kDa band corresponding to azurin by N-terminal analysis and a 9 kDa band corresponding to cytochrome $c_{551}$. The *B. cepacia* QSFT fraction showed the presence of three predominant bands of 75 kDa, 20 kDa and 8 kDa. The N-terminal amino acid sequence of 10 amino acids of the 20 kDa band (AHHSVDIQGN), determined by Edman degradation, showed 80% sequence homology to that of the N-terminal 10 amino acid sequence of *P. aeruginosa* azurin while the N-terminal amino acid sequence of 10 amino acids of the 8 kDa band (EDPEV-LFKNK) showed 100% match with that of *P. aeruginosa* cytochrome $c_{551}$. Thus the QSFT fractions having high cytotoxic activity of both *P. aeruginosa* and *B. cepacia* show enrichment with azurin and cytochrome $c_{551}$ type of redox proteins. In contrast, the *M. bovis* QSFT fraction showed a thick 65 kDa band of bovine serum albumin (BSA), which is a constituent of the 7H9 medium used for growing *M. bovis*, as well as several bands of greater than 45 kDa molecular mass, but not the 8 kDa or 22 kDa cytochrome $c_{551}$ or azurin type of proteins.

Example 10

Cell Death in Macrophages Treated with Azurin/Cytocbrome $c_{551}$

Purified azurin and cytochrome $c_{551}$ (Sigma Chemicals, St. Louis U.S.A.) were added to macrophages, prepared as in Example 2, and the mixture incubated for 2 hrs. Azurin and cytochrome $c_{551}$ concentrations were as in FIG. 4. The numbers represent μg protein. Macrophage cell death was measured by the release of the intracellular enzyme lactate dehydrogenase (LDH) using the method of Example 2. Both azurin and cytochrome $c_{551}$ caused macrophage cell death. A combination of azurin and cytochrome $c_{551}$ caused more extensive macrophage cell death. The buffer control (buffer) is shown at right. (FIG. 4).

Example 11

Induction of Apoptosis in Macrophages Treated with Azurin/Cytochrome $c_{551}$

Macrophage isolation was as in Example 2. The macrophages were treated with azurin/cytochrome $c_{551}$ (50/25 μg) for 4 and 6 hours and then examined by confocal microscopy, using the ApoAlert Mitochondria Membrane Sensor kit as in Example 4, to determine the extent of apoptosis. Macrophages underwent increasing levels of apoptosis with increasing periods of incubation in presence of azurin/cytochrome $c_{551}$ mixture. Control macrophages without treatment (treated with phosphate-buffered saline for 6 hours) did not show apoptosis.

Example 12

Cytotoxicity of an Azurin/Cytochrome $c_{551}$ Mixture or the QSFT Fractions Derived from *B. cepacia* or *M. bovis* in Macrophages after Pretreatment with Anti-azurin and Anti-cytochrome $c_{551}$ Antibodies Macrophage isolation was as in Example 2. Macrophages were treated with a purified azurin/cytochrome $c_{551}$ mixture (50/25 μg), or the *B. cepacia* or *M. bovis* QSFT fractions in the presence and absence of a mixture of anti-azurin and anti-cytochrome $c_{551}$ antibodies prepared in rabbits. Antibodies were mixed in a ratio of 1:1 and the mixed antibody (1, 2, 3, or 4 mg) was used for treatment of macrophages.

The extent of macrophage cell death was determined by release of the LDH as in Example 2. FIG. 5 shows a reduction of cytotoxicity towards macrophages treated with an azurin/cytochrome $c_{551}$ mixture (A+C), or the QSFT fraction derived from *B. cepacia* (Bc-QSFT), when anti-azurin and anti-cytochrome $c_{551}$ antibodies are present. This reduction was not observed with the QSFT fraction from *M. bovis* (Mb-QSFT).

Hence, when an azurin/cytochrome $c_{55}$; mixture or the *B. cepacia* QSFT fraction was treated with a mixture of anti-azurin and anti-cytochrome $c_{551}$ antibodies, and then assayed for macrophage cytotoxicity, the cytotoxicity was greatly diminished. In contrast, when the *M. bovis* QSFT fraction, which was previously shown by SDS-PAGE gel to lack azurin and cytochrome $c_{551}$ bands (Example 9), was pretreated with anti-azurin/anti-cytochrome $c_{551}$ antibodies and then assayed for cytotoxicity, very little reduction in cytotoxicity was observed.

Example 13

Induction of Apoptosis in Tumor Cell Lines by the *B. cepacia* QSFT Fraction and by Azurin/Cytochrome $c_{551}$ as Measured by Confocal Microscopy H460 lung carcinoma, PA-1 ovarian cancer, NCF breast cancer, HT-29 colon cancer and HT-1080 leukemia cell lines were obtained from the American Type Culture Collection (Manassas, Va., U.S.A.). MDD7 and MN1 breast cancer cell lines were obtained from Andrei Gudkov, Ph.D., Cleveland Clinic Foundation (Cleveland, Ohio U.S.A.). UISO-BCA-9 breast cancer and USIO-MEL-1, MEL-2. MEL-6 and MEL-29 melanoma cell lines were developed and maintained as described in Rauth, S et al. In vitro Cellular and Developmental Biology, 30a(2): 79-84 (1994) and Rauth, S et al., Anticancer Research, 14(6): 2457-2463 (1994). Approximately $1\times10^5$ of each cell type were cultured overnight in a 0.15 mm thick dTC3 dish (Bioptech, Butler, Pa. U.S.A.) in the presence of the *B. cepacia* QSFT fraction (5 μg protein) or a azurin/cytochrome $c_{551}$ mixture (50/25 μg). The cells were subsequently examined by confocal microscopy, as in Example 4, to determine the extent of apoptosis. Both the *B. cepacia* QSFT fraction the and azurin/cytochrome $c_{551}$ mixture induced extensive apoptosis in H460 lung carcinoma. HT-29 colon cancer, HT-1080 leukemia, PA-1 ovarian cancer, MDD7, NCF and MN1 breast cancer, and USIO-MEL-1, MEL-2, MEL-6 and MEL-29 melanoma cells after overnight incubation. In each case, cells not treated with cytotoxic factor (phosphate-buffered saline added) did not show extensive apoptosis.

Example 14

Induction of Apoptosis in USIO-Mel-6 Melanoma Cell Line by the *M. bovis* QSFT Fraction as Measured by TUNEL Assay USIO-Mel-6 melanoma cells were prepared as described in Rauth, S et al., Anticancer Research, 14(6): 2457-2463 (1994). *M. bovis* QSFT fraction was prepared as in Example 8. The melanoma cells treated with *M. bovis* QSFT fraction (5 μg protein) and untreated control cells were incubated for 12 hours. Induction of apoptosis was measured using the TUNEL assay to detect apoptosis-induced nuclear DMA fragmentation as in Example 8. Melanoma cells treated with the *M. bovis* QSFT fraction showed a yellow-green nucleus

Example 15

Reduction of Growth of Melanoma Tumor Cells (USIO-Mel-2) in Nude Mice after Treatment with Azurin/Cytochrome $c_{551}$ Approximately $10^6$ USIO-Mel-2 cells were injected subcutaneously in nude mice (available from Frederick Cancer Research and Development Center, Frederick, Maryland U.S.A.). Small tumors developed after approximately three weeks. The mice then received once weekly intraperitoneal injections of a known anti-melanoma drug, DTIC [5(3,3'-N,N-dimethyl triazen-1-yl)-imidazole-4-carboxamide] (7.5 µg) (see Ahlmais et al., Cancer 63: 224-7 (1989)) or three weekly intraperitoneal injections of a high (150 µg azurin/75 µg cytochrome $c_{551}$), low (10 µg azurin/5 µg cytochrome $c_{551}$) dose of azurin/cytochrome $c_{551}$ mixture or control (citrate buffer) for 4 weeks. The tumor volume was determined at intervals in the control, DTIC-treated, and high and low dose azurin/cytochrome $c_{551}$-treated mice.

Figure 6:
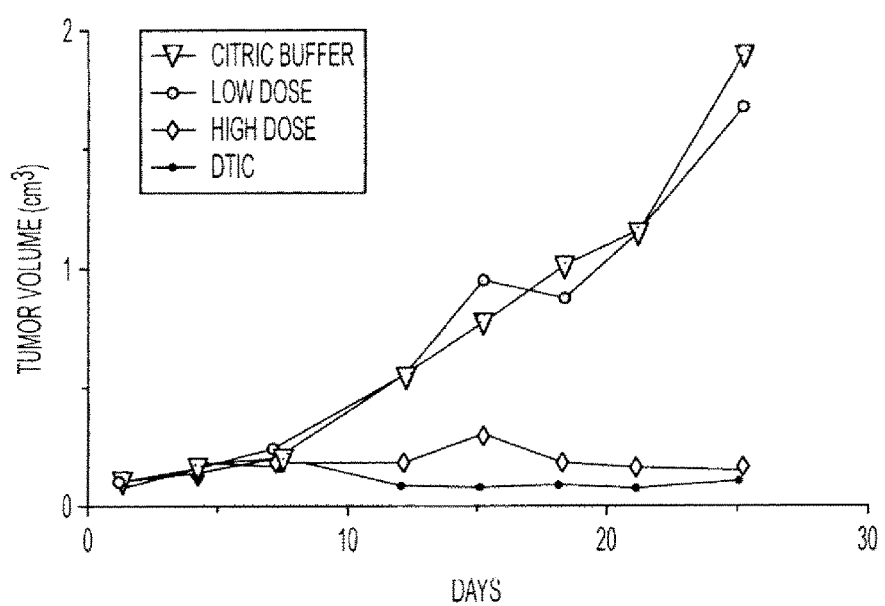
FIG. 6. Graph showing the effect of post injection of azurin/cytochrome $c_{551}$ in nude mice on the size of the tumor after induction of melanoma tumor cells (UISO-Mel-2). Approximately $10^6$ UISO-Mel-2 cells were injected subcutaneously in nude mice followed by once weekly intraperitoneal injections of either citrate buffer (control), a known anti-melanoma drug DTIC (7.5 µg) or three times per week a high (150 µg azurin/75 µg cytochrome $c_{551}$) or low (10 µg azurin/5 µg cytochrome $c_{551}$) dose of azurin/cytochrome $c_{551}$ mixture for 4 weeks. At various times, the sizes (tumor volume) of the tumors in control (buffer treated), DTIC-treated and high and low dose azurin/cytochrome $c_{551}$-treated mice were determined and plotted graphically.
Figure 7:
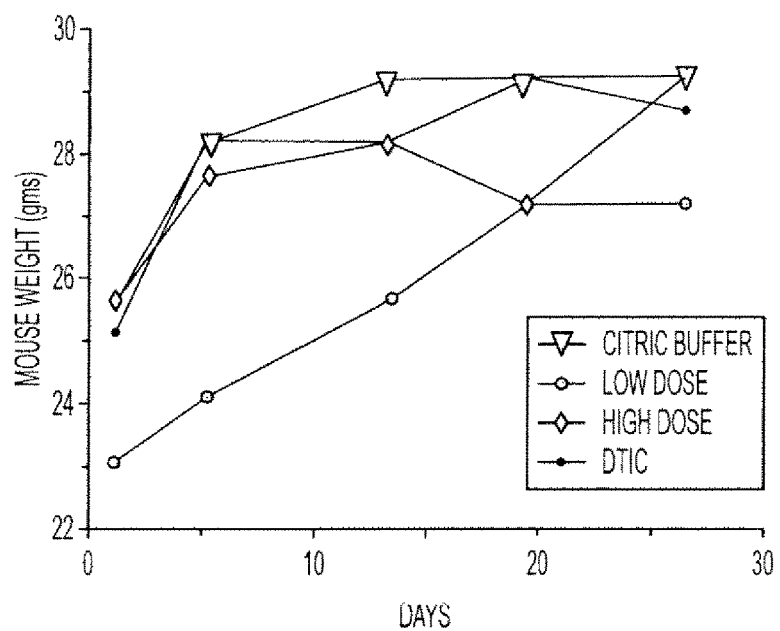
FIG. 7. Graph showing gain or loss of weight of the mice during the experiment described under FIG. 6. During the course of the above experiment, the mice were weighed on a scale and the weights in grams noted.

The increases in tumor size in control, DTIC-treated and azurin/cytochrome-treated nude mice are shown in FIG. 6 and the weight gain/loss data in such mice are shown in FIG. 7. Post-injection of a high dosage of 150 µg azurin/75 µg cytochrome-$c_{551}$ produced delayed growth and a shrinkage of the tumor size comparable of DTIC. FIG. 7 shows that the injection of either DTIC or azurin/cytochrome $c_{551}$ mixture did not affect the weight gain of the mice. All mice gained weight during the experimental period.

Example 16

Effect of Post Injection of Azurin and *M. bovis* QSFT Fraction in Nude Mice on Tumor Size after Injection of Melanoma Tumor Cells (Mel-6)

Figure 8:
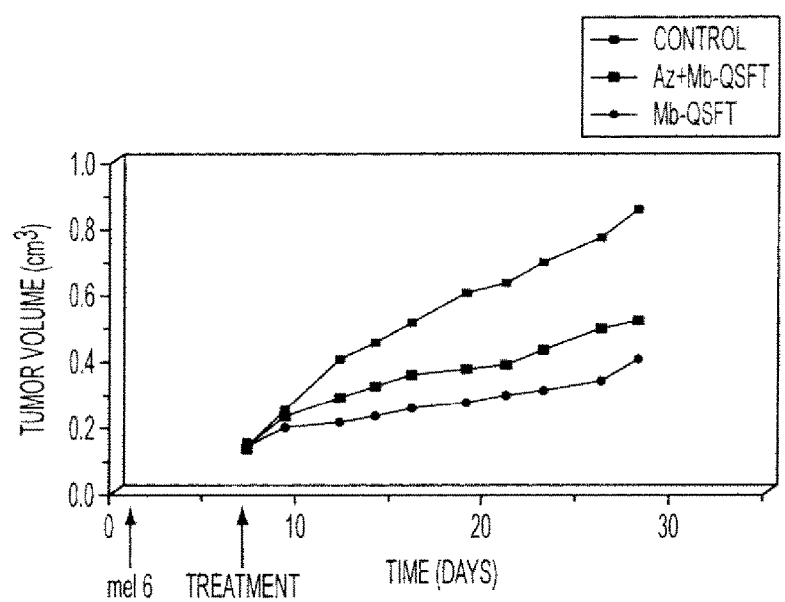
FIG. 8, Graph showing regression of Mel-6 tumor in nude mice treated with *M. Bovis* QSFT fraction in the presence or absence of azurin (AZ). Approximately $10^6$ UISO-Mel-6 cells were injected subcutaneously in nude mice. Small tumors developed after approximately one week. The mice were then intraperitonealy injected with phosphate buffered saline (control), *M. Bovis* QSFT fraction or a mixture of *M. Bovis* QSFT fraction and azurin.

Approximately $10^6$ USIO-Mel-6 cells were injected subcutaneously in 3 nude mice (available from Frederick Cancer Research and Development Center, Frederick, Md. U.S.A.). Small tumors developed after approximately three weeks. One mouse was then injected intraperitoneally with phosphate-buffered saline (control), one mouse was injected with *M. bovis* QSFT fraction (5 µg protein) and one mouse was injected with a mixture of *M. bovis* QSFT fraction (5 µg protein) and Azurin (50 µg). The *M. bovis* QSFT fraction was prepared as in Example 8. The sizes (tumor volume) of the tumors in control, *M. bovis* QSFT fraction treated and *M. bovis* QSFT fraction/Azurin treated mice were determined over a period of 30 days. These data are shown in FIG. 8. Both the treated nice showed decreased tumor growth compared to the control mouse.

What is claimed is:

1. A pharmaceutical composition comprising:
cytotoxic factors comprising an azurin and a cytochrome $c_{551}$; and a pharmaceutically-acceptable carrier;
wherein the dosage form is selected from the group consisting of: a tablet, a pill, a dragee and a gel; and
wherein the cytotoxic factors are present in a therapeutically effective amount to cause the death of cancer cells in the patient, or inhibit the growth of cancer cells in the patient.

2. The pharmaceutical composition of claim 1, wherein the azurin is from *Pseudomonas aeruginosa*.

3. The pharmaceutical composition of claim 1, wherein the cancer cells are selected from the group consisting of: melanoma cells, leukemia cells, breast cancer cells, ovarian cancer cells, lung cancer cells, mesenchymal cancer cells, colon cancer cells, and aerodigestive tract cancer cells.

4. The pharmaceutical composition of claim 1 wherein the dosage form is suitable for administering to the patient by oral, buccal, sublingual, rectal, vaginal, transurethral, nasal, topical, percutaneous, transdermal, intramuscular, or subcutaneous administration.

5. A method of making a dosage form for administration to a patient with cancer comprising combining an azurin and a cytochrome $c_{551}$ in an admixture with a pharmaceutically acceptable carrier; and making the admixture into a dosage form selected from the group consisting of a tablet, a pill, a dragee, a capsule and a gel, wherein the cytotoxic factors are present in the dosage form in an amount to cause to cause the death of cancer cells in a patient, or inhibit the growth of cancer cells in a patient.

6. The method of claim 5 wherein the dosage form is suitable for administering to a patient by oral, buccal, sublingual, rectal, vaginal, transurethral, nasal, topical, percutaneous, transdermal, intramuscular, or subcutaneous administration.

* * * * *